US009055973B2

(12) United States Patent
Varma (10) Patent No.: US 9,055,973 B2
(45) Date of Patent: Jun. 16, 2015

(54) DEVICE TO ASSIST IN CESAREAN SECTION

(76) Inventor: Rajiv Varma, Essex (GB)

( * ) Notice: Subject to any disclaimer, the term of this patent is extended or adjusted under 35 U.S.C. 154(b) by 455 days.

(21) Appl. No.: 11/815,807

(22) PCT Filed: Oct. 11, 2005

(86) PCT No.: PCT/GB2005/003902
§ 371 (c)(1),
(2), (4) Date: Aug. 8, 2007

(87) PCT Pub. No.: WO2006/085045
PCT Pub. Date: Aug. 17, 2006

(65) Prior Publication Data
US 2008/0154284 A1    Jun. 26, 2008

(30) Foreign Application Priority Data
Feb. 8, 2005    (GB) .................................. 0502546.5

(51) Int. Cl.
*A61B 17/42* (2006.01)
*A61B 17/44* (2006.01)

(52) U.S. Cl.
CPC ............... *A61B 17/442* (2013.01); *A61B 17/42* (2013.01)

(58) Field of Classification Search
CPC .............................. A61B 17/442; A61B 17/42
USPC ......... 1/122; 606/191, 192, 193, 122; 600/29, 600/30, 31, 32; 138/93; 220/232; 277/331, 277/583, 605, 646
See application file for complete search history.

(56) References Cited

U.S. PATENT DOCUMENTS

| | | | | |
|---|---|---|---|---|
| 713,708 A | * | 11/1902 | Spire | 215/269 |
| 3,106,441 A | * | 10/1963 | Harrison et al. | 156/221 |
| 3,480,017 A | * | 11/1969 | Shute | 606/193 |
| 4,018,230 A | | 4/1977 | Ochiai et al. | |
| 4,207,891 A | * | 6/1980 | Bolduc | 128/831 |
| 4,338,943 A | | 7/1982 | Okamoto et al. | |
| 4,480,424 A | * | 11/1984 | Seldon | 53/489 |
| 5,307,811 A | * | 5/1994 | Sigwart et al. | 600/490 |
| 5,308,327 A | * | 5/1994 | Heaven et al. | 604/103.09 |

(Continued)

FOREIGN PATENT DOCUMENTS

| | | | |
|---|---|---|---|
| DE | 10038469 A1 | 2/2002 | |
| WO | 01/10493 A1 | 2/2001 | |
| WO | WO 2005/030064 | * 9/2004 | A61B 17/42 |

OTHER PUBLICATIONS

Hager et al, Complications of Cesarean Deliveries: Rates and Risk Factors, Feb. 2004, American Journal of Obstetrics and Gynecology, vol. 190, Issue 2, pp. 428-434.

(Continued)

*Primary Examiner* — Kathleen Holwerda
*Assistant Examiner* — Sarah Simpson
(74) *Attorney, Agent, or Firm* — Cohen & Hildebrand, PLLC (57) ABSTRACT

Surgical device to allow an easy delivery of the fetus during a Cesarean Section when fetal head is deeply wedged in the female pelvic cavity. The device consists of inflatable portion to lift the fetal head attached to foldable base plate that can be folded with the inflatable portion for insertion of the device into the female vagina below the fetal head. The inflatable portion is inflated by injecting biocompatible fluid by pressurizing device such as syringe, pressure bag, hand pump or powdered pump. The device can also be of use in other situations like abdominal delivery of a premature or small baby and when cord prolapse has occurred.

18 Claims, 11 Drawing Sheets

(56) References Cited

U.S. PATENT DOCUMENTS

| | | | |
|---|---|---|---|
| 6,355,047 | B1 | 3/2002 | Wallace et al. |
| 6,648,842 | B2 * | 11/2003 | Horkel .......................... 601/45 |
| 7,018,392 | B2 * | 3/2006 | Hudson et al. ................. 606/192 |
| 2002/0010441 | A1 * | 1/2002 | Horkel .......................... 604/279 |
| 2002/0183779 | A1 * | 12/2002 | Vigil ............................ 606/192 |
| 2004/0059289 | A1 * | 3/2004 | Garza Alvarez ........... 604/96.01 |

OTHER PUBLICATIONS

Fasubaa et al, Delivery of the Impacted Head of the Fetus at Caesarean Section After Prolonged Obstructed Labour: A Randomized Comparative Study of Two Methods, Jul. 2002, Journal of Obstetrics and Gynaecology, vol. 22, No. 4, pp. 375-378.

Landesman et al, Abdominovaginal Delivery: Modification of the Cesarean Section Operation to Facilitate Delivery of the Impacted Head, Mar. 15, 1984, American Journal of Obstetrics and Gynecology, vol. 148, No. 6, pp. 707-710.

Blickstein, Difficult Delivery of the Impacted Fetal Head During Cesarean Section: Intraoperative Disengagement Dystocia, 2004, Journal of Perinatal Medicine, vol. 32, No. 6, pp. 465-469.

Arad et al, Vacuum Extraction at Cesarean Section—Neonatal Outcome, 1986, Journal of Perinatal Medicine, vol. 14, No. 2, pp. 137-140.

Bader et al, Maternal and Fetal Catecholamines and Uterine Incision-to-Delivery Interval During Elective Cesarean, Apr. 1990, Obstetrics & Gynecology, vol. 75, No. 4, pp. 600-603.

Khosla et al, Cesarean Section In a Wedged Head, May 2003, Indian Journal of Medical Sciences, vol. 57, No. 5, pp. 187-191.

Ekele, Disengaging Impacted Head at Caesarean Section for Obstructed Labour—Push or Pull?, Jan. 31, 2001, Tropical Doctor, Short Reports, vol. 31, No. 1, pp. 38-39.

Demott et al, The Green Bay Cesarean Section Study: II. The Physician Factor as a Determinant of Cesarean Birth Rates for Failed Labor, Jun. 1992, American Journal for Obstetrics and Gynecology, vol. 166, Part 1, pp. 1799-1810.

Murphy et al, Early Maternal and Neonatal Morbidity Associated with Operative Delivery In Second Stage of Labour: A Cohort Study, Oct. 13, 2001, The Lancet, vol. 358, pp. 1203-1207.

Murphy, K.W. In: Bonnar J, Editor, "Reducing the Complications of Cesarean Section", Recent Advances in Obstetrics and Gynaecology, London: Churchill Livingstone (1999), p. 144-152.

Mukhopadhyay et al., "Evaluation of Patwardhan's Technic—a four year study in a rural teaching hospital," The Journal of Obstetrics and Gynecology of India, vol. 55, No. 3, May/Jun. 2005, pp. 244-246.

* cited by examiner

DEVICE TO ASSIST IN CESAREAN SECTION

TECHNICAL FIELD OF THE INVENTION

The present invention relates to a surgical device and its method of use, particularly for use in carrying out a Cesarean Section to deliver the baby when vaginal birth is not possible due to various reasons.

BACKGROUND OF THE INVENTION

In last two decades, incidence of Cesarean Section (delivery through an abdominal incision) has been constantly rising at a high rate. In UK and other western countries, the average rate of Cesarean Section is around 25% and continues to increase. A significant proportion of Cesarean Sections are performed during second stage or when women are in late stages of labour. Along with these statistics there are been a rising trend in failed instrumental deliveries, adding to this group of patients. There is evidence that Cesarean Section performed in these circumstances is prone to higher complications both for the baby and the mother.

The mechanism of difficult delivery of the fetal head during a Cesarean Section is not entirely clear. However, it is clear that such situations rarely, if ever, exist in elective Cesarean Section. It follows that the impaction of fetal head is a manifestation of an advanced first stage, and much more likely, an event of the second stage.

Moreover, the impaction seems to be more likely when the second stage is unduly prolonged. Clinician has to decide in these circumstances whether to try an instrumental vaginal delivery or carry out a Cesarean Section. Therefore, some of these cases can be due to a reluctance to perform an instrumental delivery. The greater use of Cesarean Section and the reduction in instrumental deliveries has compounded this problem.

There is also an increased use of epidural analgesia in labour often resulting in a prolonged second stage of labour due to lack of maternal urge to push. This could be another mechanism for the impaction of fetal head in the maternal pelvis.

The deeply engaged fetal head is likely to lead to difficulty in delivery during Cesarean Section often leading to a delay in uterine decision, delivery interval resulting in hypoxic trauma to fetus. Degree of this trauma depends on the amount of delay. There is also risk of direct injury to fetus due to force used during the attempted delivery by the operator.

The use of assistant to help in pushing the fetal head through the vaginal route has been also suggested. This technique can also cause direct trauma to the fetus and lead to delay in delivery. A higher rate of maternal trauma and infections has also been reported while using this technique.

Use of the vacuum instrument recommended in this situation, it also adds to delay in delivery of an already compromised fetus. Other techniques described are breech extraction, which is often difficult and traumatic unless the operator is familiar with it.

Extension of uterine incision is quite common when the Cesarean Section is carried out at late stage of labour, incidence of around 35% has been reported. This often leads to increased blood loss and need for blood transfusion and higher risk of trauma to urinary tract during attempts to repair this.

Medicolegal risks of second stage Cesarean Section are significant. The Royal College of Obstetricians and Gynecologists (U.K.) have suggested that there should be more experienced help at hand when such a situation arises (Sentinel Audit).

To address above mentioned problems in child birth it would be beneficial to have a device which can be used for assisting obstetrician in a delivery of fetus during a Cesarean Section. This device could be of substantial benefit to the patient and could also be used in the situation when a cord prolapse has occurred, thus allowing the fetal head to be pushed up thereby allowing more time to prepare for an emergency Cesarean Section.

Such an invention could also be useful when performing Cesarean Section in premature or small babies and could be novel in use for dislodging the fetal head which is deeply wedged in the pelvic cavity and to deliver fetus without undue delay and trauma that could be beneficial for baby.

Hence there is clear need for a device, which can dislodge or push the fetus head up in the uterus and facilitate the delivery in a non-traumatic or safe fashion.

The present invention is novel and relates to use of a device to assist surgeon in performing a Cesarean Section.

SUMMARY OF INVENTION

The present invention comprises a novel surgical instrument for assisting in a Cesarean Section. It is an advantage of the current invention to provide a gentle force to assist the surgeon to dislodge the fetal head that is deeply wedged in the pelvic cavity and to deliver fetus without undue delay and trauma.

The invention relates, in general, to a device for assisting obstetrician during a Cesarean Section. The invention is particularly but not exclusively concerned with supporting and pushing the fetal head up in the pelvis just before a Cesarean Section is attempted. This may be done to dislodge the deeply engaged fetal head and push it in a manner, which will assist a surgeon to safely deliver the baby. This could also be beneficial in other surgical operations.

It is another advantage of the invention to provide the necessary lift for the fetus when an unsuccessful attempt has already been made to deliver the baby vaginally using forceps or vacuum instruments.

Another advantage is to prevent having to deliver the fetal body before delivering the head during a Cesarean Section when the head is impacted or wedged in the pelvis.

Still another advantage of the present invention is to reduce the need for an assistant or the surgeon to push the fetus from below when the fetal head is wedged in the pelvic cavity, when performing a Cesarean Section.

Yet another advantage of the invention is to prevent trauma to the uterus when delivering the fetus by Cesarean Section in a situation when the fetus is very low in the pelvis.

In order to achieve general aspect of the present invention, the device consists of an inflatable portion as a main component, which acts as a hydraulic jack to lift the fetal head when it is impacted in the pelvis.

BRIEF DESCRIPTION OF THE DRAWINGS

A complete understanding of the present invention may be obtained by reference to the accompanying drawings, when considered in conjunction with the subsequent detailed description, in which.

DETAILED DESCRIPTION OF PREFERRED EMBODIMENT

The present invention is not limited to the particular shape disclosed. It is expressly understood that a large number of different sizes, shapes and dimensions of both the inflatable portion and plate can be made. The device can also comprise of an inflatable portion only, without the need for a separate base plate. Following description is meant to be illustrative only and not limiting. Other embodiments of this invention will be apparent to those of ordinary skill in the art, in view of this description.

Figure 1:
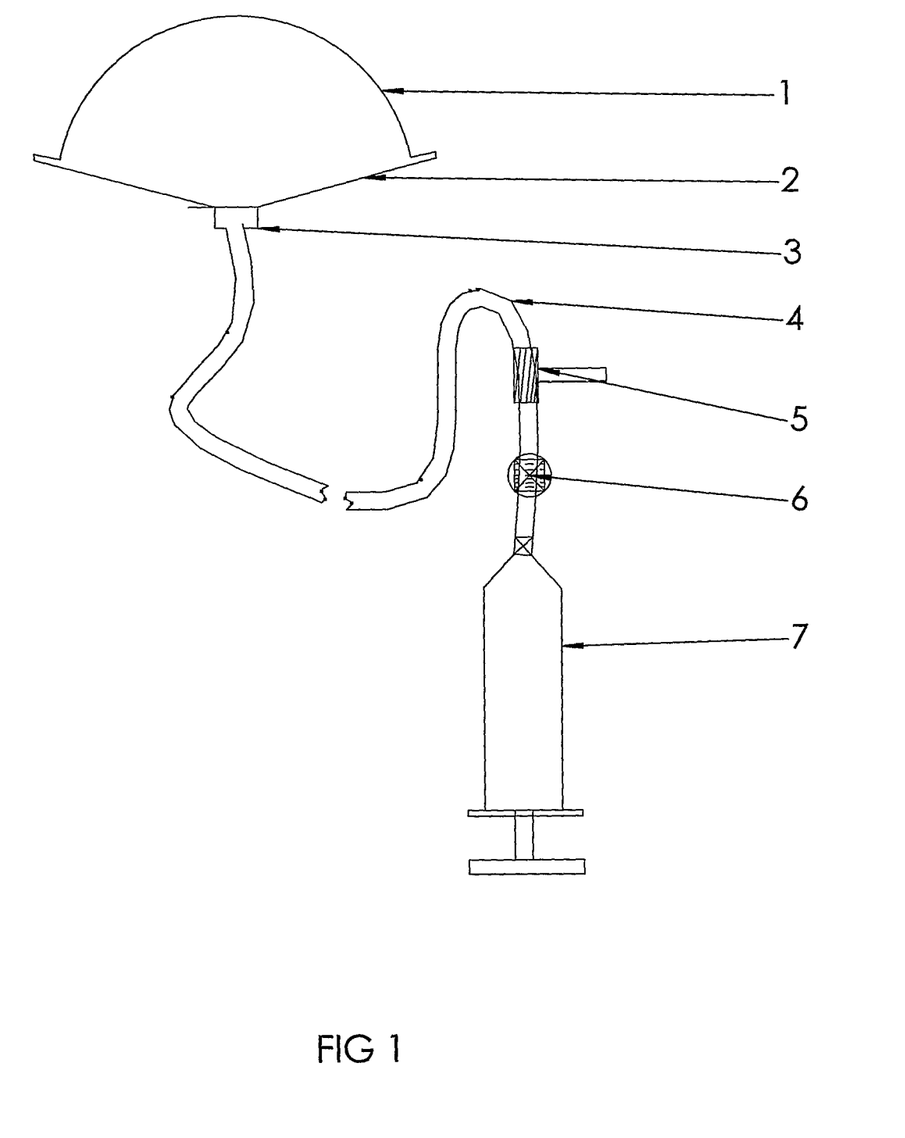
FIG. 1 complete device with the inflated inflatable portion
Figure 2:
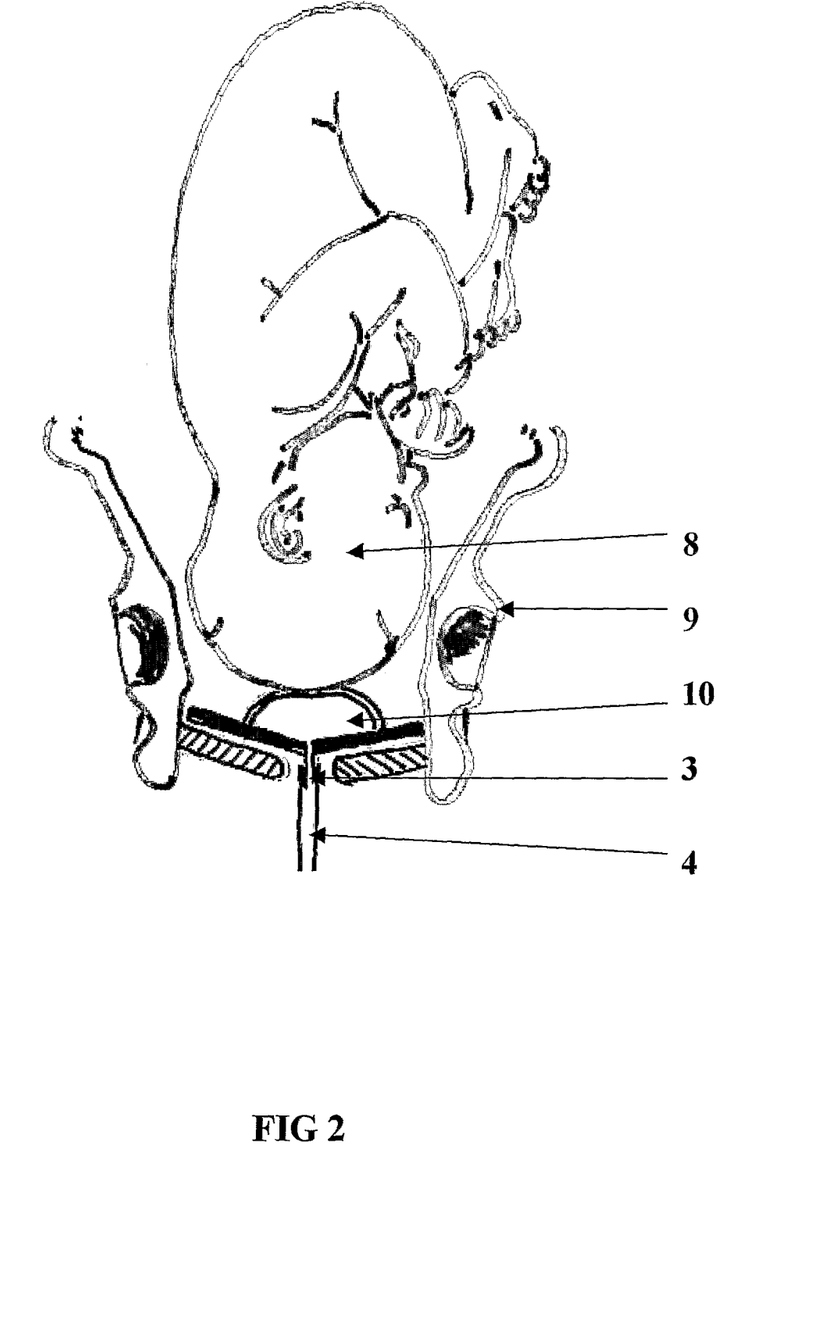
FIG. 2 cross section of inflated device placed under the fetal head.
Figure 3:
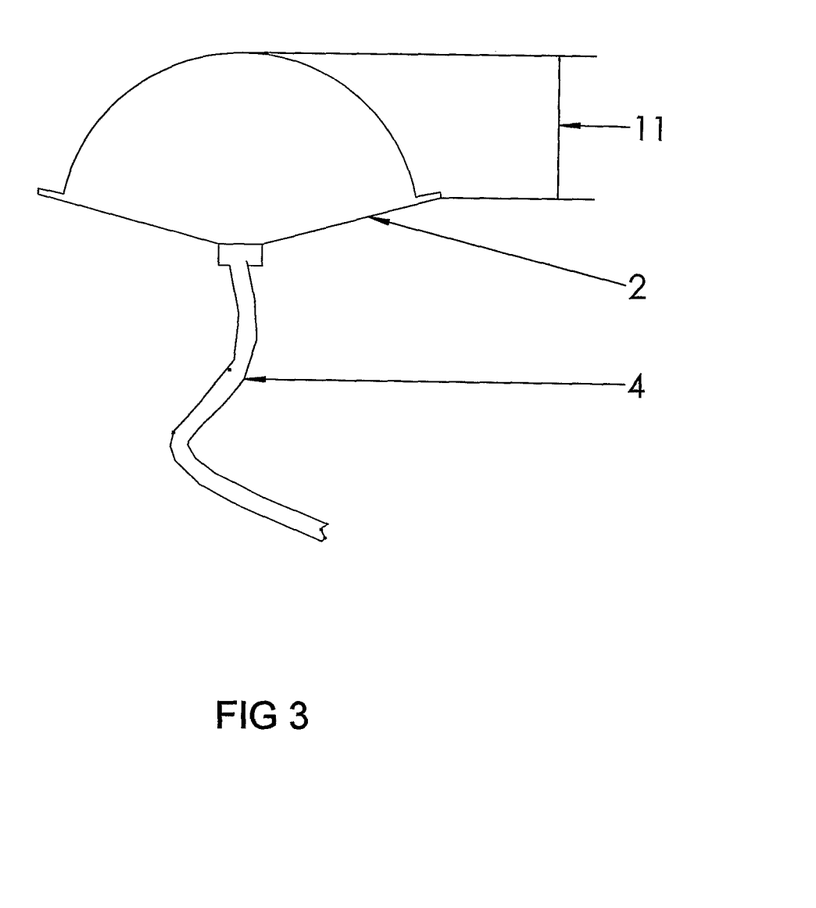
FIG. 3 longitudinal section view of complete inflated device taken through the long axis.
Figure 4:
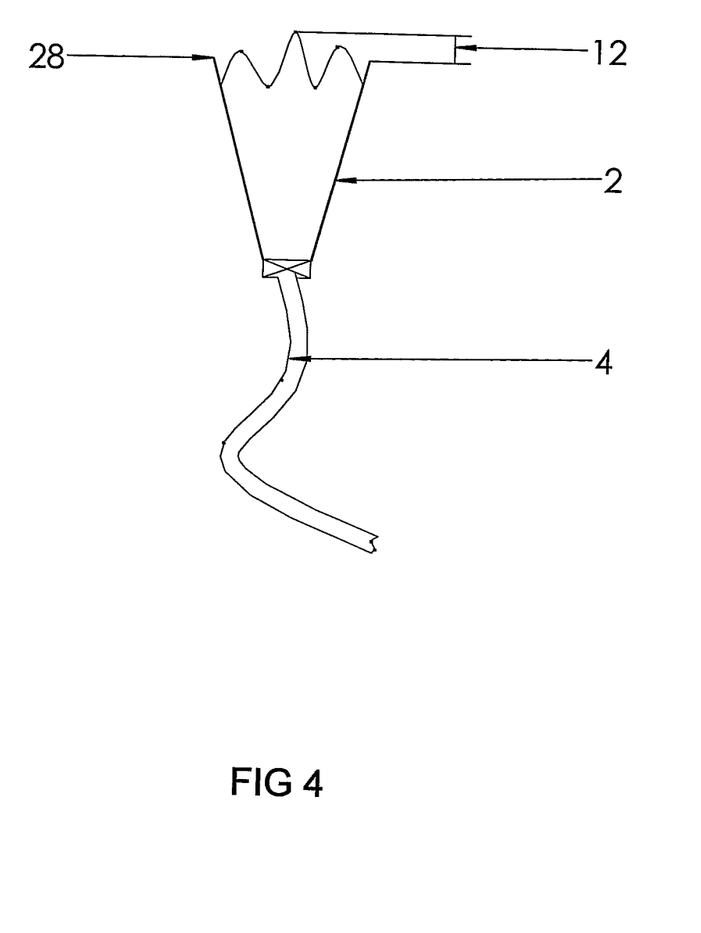
FIG. 4 longitudinal section view of complete deflated device taken through the long axis.
Figure 5:
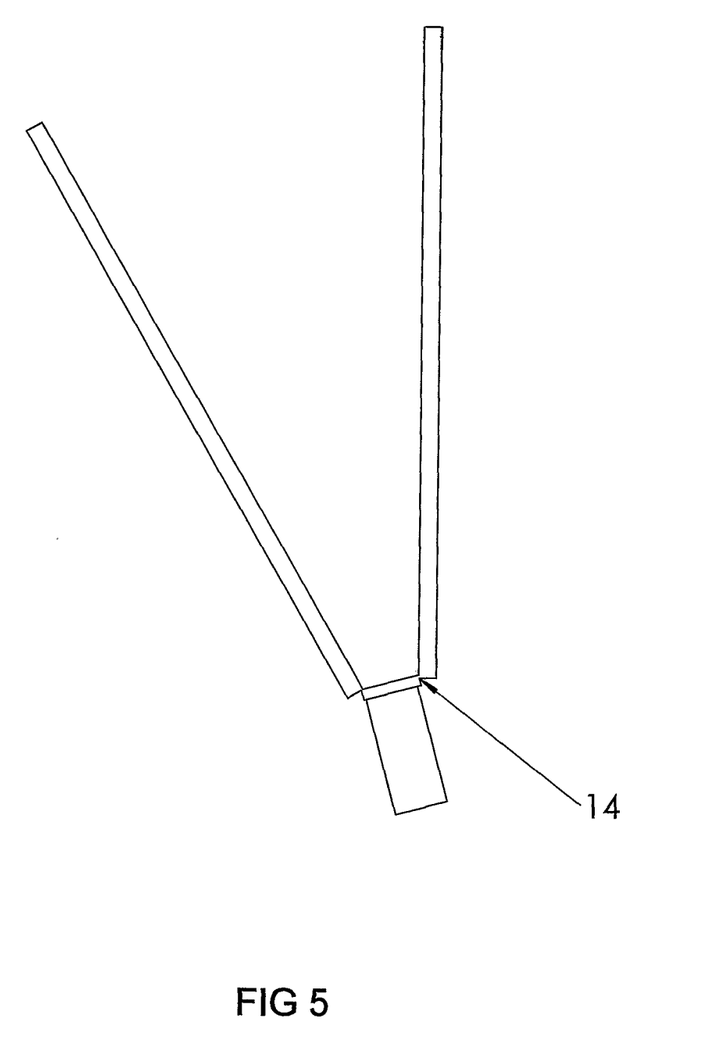
FIG. 5 illustrates the detailed view of the folding mechanism of the base plate.
Figure 6:
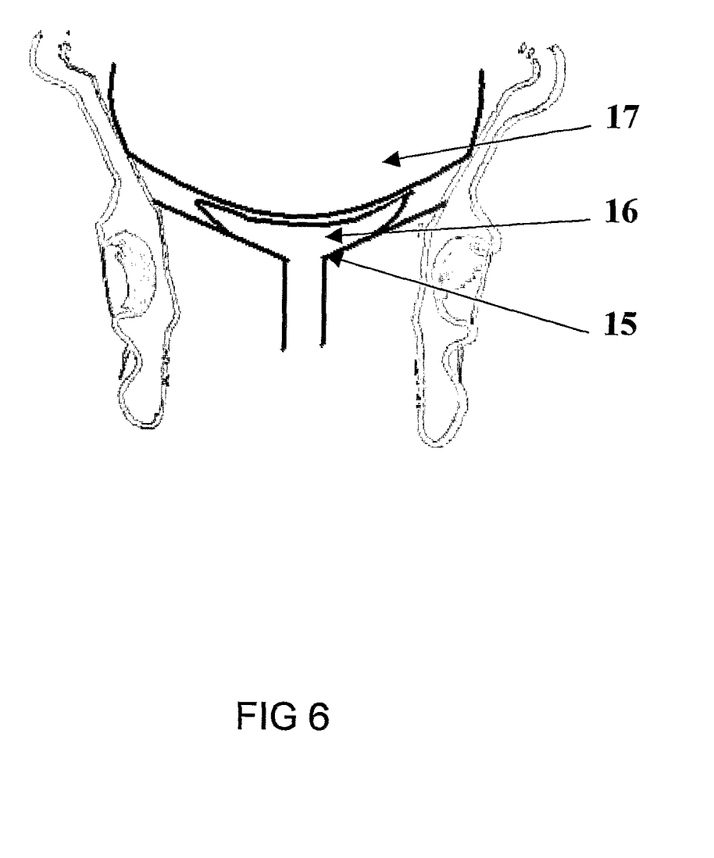
FIG. 6 schematic representation of the deflated device inserted below the impacted fetal head.
Figure 7:
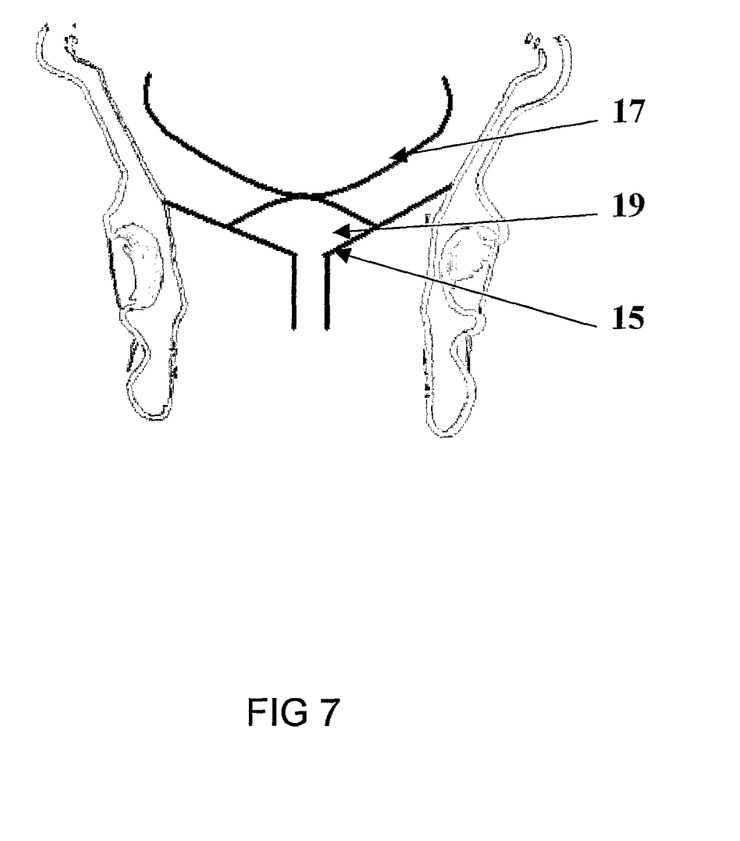
FIG. 7 schematic representation of the fully inflated device showing the fetal head disimpacted from the pelvic cavity.
Figure 8:
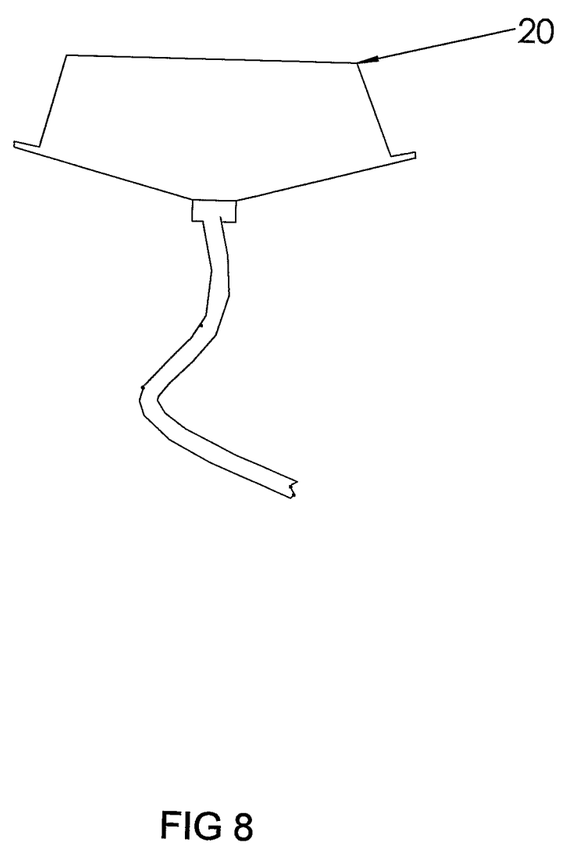
FIG. 8 represent one possible shape of inflatable portion
Figure 9:
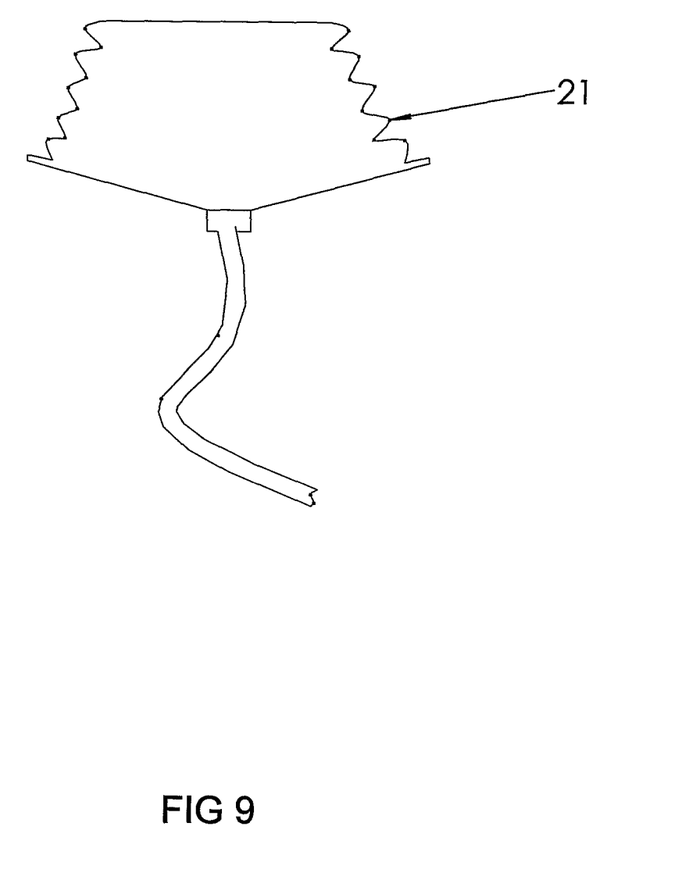
FIG. 9 represents one more possible shape of inflatable shape
Figure 10:
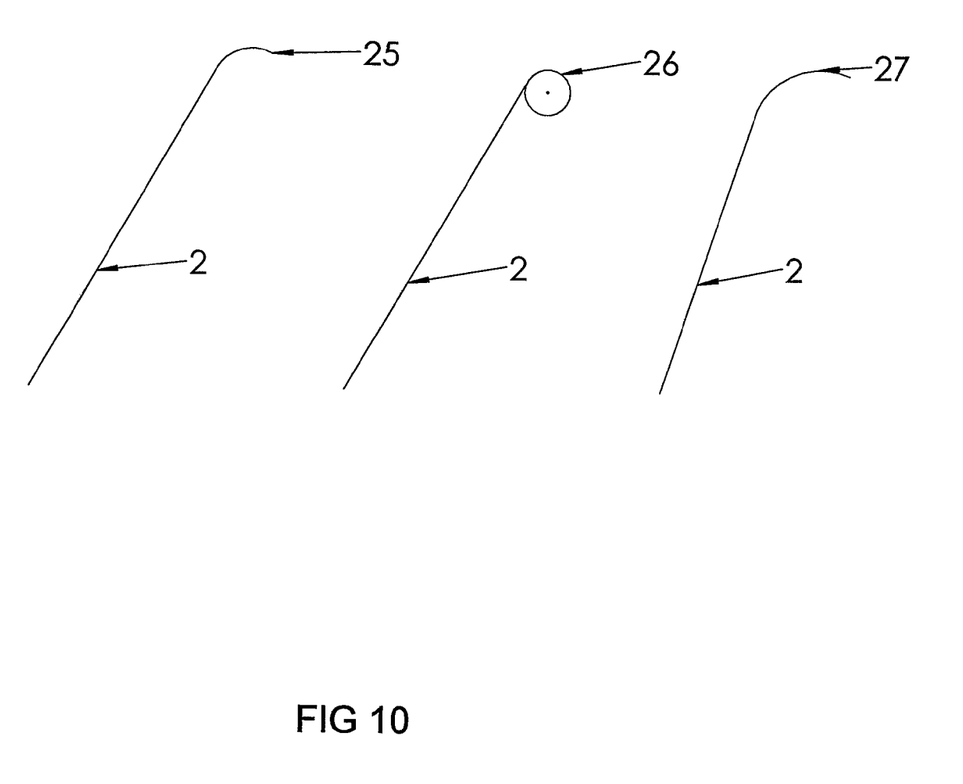
FIG. 10 represents different shapes of edges, which may reduce trauma
Figure 11:
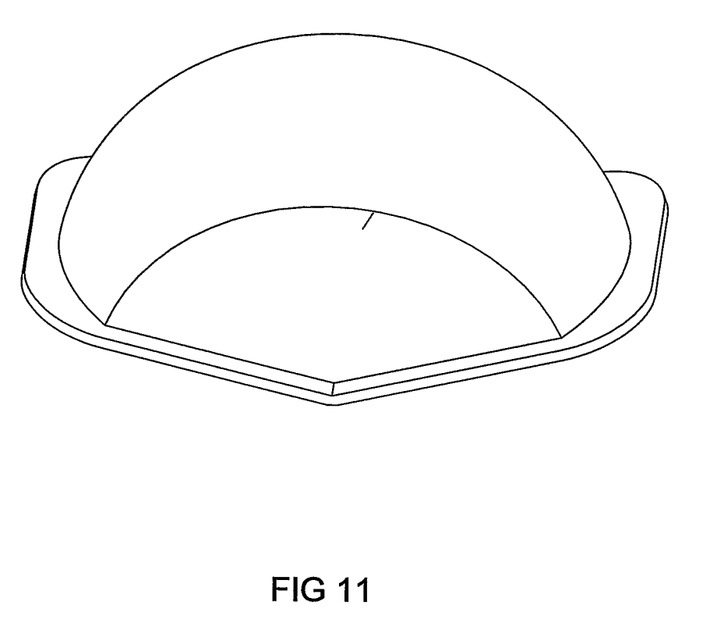
FIG. 11 represents a 3D sketch of the inflatable portion and plate of the device for better understanding of the invention.

The inflatable portion (1) can be in the shape of balloon, dome, bellow, square, trapezoid or combination thereof. The inflatable portion is mounted on the plate (2) by sticking to it by appropriate adhesive or by mechanical joints or by heat sealing or fusing it to the plate or made as one part or combination thereof. The inflatable portion is made a part of the plate such that the inflatable portion will not get unintentionally disconnected from the plate during usage. The inflatable portion (1) can be mounted permanently, semi permanently or temporarily on the plate. The plate (2) has a hole in the middle to allow the connecting tubing (4) to be attached to the Inflatable portion for its inflation. The tubing can be attached by using the connector (3). The base portion of the device is a plate (2) to which the inflatable portion is attached on the superior surface by any mechanism mentioned above. This plate can be of any size or shape so as to allow it to anchor itself to the pelvic floor muscles or ligaments. The plate has to be a firm material, which is biocompatible. The edges (28) of this plate need to be either soft or rounded so as to be least traumatic to the maternal tissues. Different shapes of the plate edges are shown in side view in FIG. 10, wherein (25), (26), and (27) represent different atraumatic edge shapes. There are different shapes possible to make the edge (28) atraumatic. The plate should be able to be folded in at least one direction so as to allow the device to be squeezed into a smaller size and shape for its insertion into the vaginal below the fetal head. The base plate (2) also has a simple mechanism, which allows it to be folded in the middle along the short axis; this can be in the form of a thinner area (14) in FIG. 5, in the plate itself or any other mechanism. As shown in FIG. 1, the base plate (2) is rigid or semi-rigid plate and the plate is designed in such a way that the plate can be folded only in one direction towards the superior surface and is fixed in 180 degree angle or flat in the opposite direction. The base plate (2) also has a simple mechanism, which allows it to be folded in the middle along the short axis; this can be in the form of a thinner area (4) in the plate itself or any other mechanism. The plate also has edges that are softer or rounded (28) to make it least traumatic to the maternal tissues when it is inserted into vagina. The device can be made without the use of base plate as well using any other mechanism, which allows the base of the inflatable portion to fix to the pelvic floor when inflated. The basic principle of using the inflatable portion as a jack to lift the fetal head is the main objective of this invention. The inflatable portion and plate material should be biocompatible at least to the extent required in all respects. The inflatable material can be elastic or other elastic polymers or it can inelastic like Polyethylene, polyurethane or semi-elastic like silicon. Similarly the plate material can be rigid like stainless steel, PEEK or ABS or can be not so rigid like PE, PU or rigid silicon. The materials here are for better understanding of the invention and do not limit the scope of the invention. As shown in FIG. 1, the inflatable portion of the device is attached to a tube to inject fluid into the inflatable portion. The tube can be an integral part of the inflatable portion of the device or can be attached separately. The other end of the tube has appropriate connector to connect the pressurizing mechanism to inject fluid into the inflatable portion. The connector can be a luer connector or an appropriate size rubber tube so that the attachment between the tube and the device is secure and leak proof under the required pressure. The pressure in the balloon can be between 50 mm hg to 3000 mm hg. Pressure relieving valve (5) is attached in line with the tube (4) such that the valve opens to relieve extra pressure when set. This is not a essential feature of the device but will be an added safety mechanism. Stopcock (6) can be opened or closed as desired. The stopcock can be opened to allow the user to push in fluid. The same can be closed to disallow the fluid from flowing out. The stopcock may be a one-way valve. The device is placed in the vagina below the fetal head as shown in FIG. 2. The device is folded in the middle to allow it to place in the vagina as shown in FIG. 4. The tubing (4) allows the device to be inflated or deflated by the surgeon as required during the surgery. As the device is inflated, the rigid portion of the device, the base plate (2) takes support along the pelvic floor. FIG. 3 and FIG. 4 represent the principle of operation of this device. When the device is deflated as shown in FIG. 4, the distance (12) between the edges and top portion of the plate is lesser than the distance (11) as shown in FIG. 3. This increase in distance pushes the fetal head up. As the inflatable portion is inflated, it helps to straighten up the plate and thereby pushing and fixing the base of the device thereby preventing it from moving in a downward direction. The inflatable portion is then inflated further to push the fetus in appropriate direction. The fluid is injected using a 60 cc syringe (7). The amount of fluid required is usually around 60-100 cc to elevate the fetal head to 2-3 cms into the pelvic cavity. The fluid may be any biocompatible fluid like saline, glucose solution, ringers lactate or gases like carbon dioxide or such like. Instead of syringe, any suitable pressurizing device may be used like pump, blood pressure cuff, pressure balloon, piston cylinder or such like. The device acts like a jack usually used in other engineering industries to lift the load or position the load in proper direction. The movement of the head has to be only minimal to achieve the desired effect of dislodging it from the impacted position. FIG. 11 represents a 3D sketch of the device for better understanding of the invention. It shows only the inflatable portion and base plate of the device as the tubing, pressuring member or suck like are self explanatory.

What I claim is:

1. A surgical device for assisting in a delivery of a fetus through an abdominal incision comprising:
    a) an inflatable portion made of an inflatable material;
    b) a plate having two edges and a hole defined therethrough; the plate is mounted to the inflatable portion forming a leak proof seal therebetween defining a space for receiving a fluid in the space defined by the leak proof seal between the plate and the inflatable portion;

the plate being foldable only along one direction in response to a change in pressure within the device; as the device is inflated and pressure therein increases, the edges of the plate are pushed further apart, while as the device is deflated and pressure therein decreases, the edges of the plate are drawn closer together; and c) a hollow tube received in the hole defined in the plate and forming a leak proof seal therebetween.

2. The surgical device in accordance with claim 1, wherein the plate is foldable to form an essentially "V" shape.

3. The surgical device in accordance with claim 1, wherein the inflatable portion inflates when filled with a fluid at a pressure higher than ambient, and subsequently deflates as the fluid escapes.

4. The surgical device in accordance with claim 3, wherein the fluid is a gas or a liquid.

5. The surgical device in accordance with claim 1, wherein a fluid is introduced into the inflatable portion via the hollow tube.

6. The surgical device in accordance with claim 1, wherein the plate is permanently attached to the inflatable portion only about its perimeter by a bond taken from the group consisting of adhesive, mechanical joint, heat seal, and fusion.

7. The surgical device in accordance with claim 1, wherein the edges of the plate are configured to be atraumatic.

8. The surgical device in accordance with claim 7, wherein the edges are curved.

9. The surgical device in accordance with claim 1, wherein the inflatable portion, when inflated, is shaped like a dome.

10. The surgical device in accordance with claim 1, further comprising as flexible hose having an inner tubular surface wherein the inner tubular surface detachably fits over the outer tubular surface of the hollow tube forming a leak proof seal therebetween to form an extended pathway for a fluid to flow to and from the device.

11. The surgical device in accordance with claim 1, further comprising a valve disposed for controlling flow of a fluid to and from the device.

12. The surgical device in accordance with claim 11, wherein the valve blocks the flow of the fluid to and from the device.

13. The surgical device in accordance with claim 1, further comprising a pressurizing device that introduces or removes a fluid into the device.

14. The surgical device in accordance with claim 13, wherein the pressurizing device is a syringe, hand pump, pressure bag, or powered pump.

15. The surgical device in accordance with claim 1, wherein the plate is foldable in a substantially centered region.

16. The surgical device in accordance with claim 1, wherein when the inflatable portion is in an inflated state, the edges of the plate extend outward beyond the inflatable portion.

17. The surgical device in accordance with claim 1 wherein the inflatable portion is attached to a superior surface of the plate; and the hollow tube has a first end and an opposite second end; the first end is received in the hole defined in the plate and forming the leak proof seal therebetween without extending beyond the plate into the inflatable portion.

18. The surgical device in accordance with claim 1, wherein the plate is sized and shaped so as to be supported by a pelvic floor when the inflatable portion is inflated.

* * * * *

UNITED STATES PATENT AND TRADEMARK OFFICE
CERTIFICATE OF CORRECTION

PATENT NO. : 9,055,973 B2  
APPLICATION NO. : 11/815807  
DATED : June 16, 2015  
INVENTOR(S) : Rajiv Varma

Page 1 of 1

It is certified that error appears in the above-identified patent and that said Letters Patent is hereby corrected as shown below:

Claims:

Col. 5, claim 10, line 2, change "as" to --a--

Signed and Sealed this
Twenty-third Day of August, 2016

Michelle K. Lee
*Director of the United States Patent and Trademark Office*